United States Patent [19]

Giordano et al.

[11]  4,328,356

[45]  May 4, 1982

[54] PROCESS FOR PREPARING ESTERS OF ARYLACETIC ACIDS FROM ALPHA-HALO-ALKYLARYLKETONES

[75] Inventors: Claudio Giordano; Francesco Casagrande, both of Novara, Italy

[73] Assignee: Montedison S.p.A., Milan, Italy

[21] Appl. No.: 121,965

[22] Filed: Feb. 15, 1980

[30] Foreign Application Priority Data

Feb. 20, 1979 [IT] Italy ................................. 20348 A/79

[51] Int. Cl.$^3$ ..................... C07C 69/76; C07C 65/105
[52] U.S. Cl. ........................................ 560/56; 560/55; 560/105; 562/465; 562/466; 568/308; 568/323; 568/328
[58] Field of Search ........................... 560/105, 56, 55; 562/465, 466

[56] References Cited

PUBLICATIONS

J. P. Bégué et al., Tetrahedron, vol. 30, pp. 141-149, (1974).
D. J. Pasto et al., J. of Organic Chem., vol. 32, pp. 778-781, (1967).
D. J. Pasto et al., J.A.C.S., 93:3, Feb. 10, 1971.

Primary Examiner—Paul J. Killos

[57]  ABSTRACT

Esters of arylacetic acids, more particularly lower alcohol esters of arylacetic acids, including those substituted on the methylene group, are prepared by rearrangement of the corresponding alpha-halo-alkylarylketones with Ag compounds in lower alcohols and in an acid medium. From the alkyl esters so prepared, their respective free acids can be obtained, if desired, by various means such as hydrolysis or the shift with mineral acids of the alkaline salts prepared by reaction with alkali, etc.

18 Claims, No Drawings

PROCESS FOR PREPARING ESTERS OF ARYLACETIC ACIDS FROM ALPHA-HALO-ALKYLARYLKETONES

BACKGROUND OF THE INVENTION

Compounds obtained according to this invention are useful for many and varied applications which are evident to the technicians in various industries.

They can be used, for example, as intermediate compounds for the further synthesis of industrial products in the field of organic chemistry in general and with particular regard to the preparation of the so-called fine chemicals, i.e., of products having a wide range of applications in perfumery, phytopharmaceutical products (phenylacetic acid), pharmaceutical products, etc., due to the presence in "alpha" position, in respect of the carboxyester or carboxylic group, of an aryl group which ensures most interesting possibilities of reaction for said compounds.

In particular, the alkyl ester, and by consequence its corresponding free acid, 2-(6'-methoxy-2'-naphthyl)-alphamethyl-acetic acid, which, for the sake of simplicity and exactness, will be hereinafter referred to as 2-(6'-methoxy-2'-naphthyl)-propionic acid, is in the form (+) adapted to use in the pharmaceutical field as anti-inflammatory, analgesic, antipyretic, anti-itching, etc., agent. Such use is widely described in the literature, as well as the relevant pharmaceutical preparations such as solutions, suspensions, pills, capsules, etc., (see, for instance, British Pat. No. 1,211,134).

Because of their versatility, several methods of preparing arylacetic acids have been proposed. For example, they can be prepared from benzyl halides or substituted benzyl halides by alkaline cyanuration and successive hydrolysis of the cyano group. Thus, 2-(4'-isobutyl-phenyl)-propionic acid, a pharmaceutical product known as "Ibuprofen", is prepared by reacting NaCN with the corresponding benzyl chloride followed by methylation and hydrolysis (U.S. Pat. No. 3,385,886).

Reactions have been described, also, according to which arylacetic acids are obtained by means of rearrangement mechanisms. For example, the Willgerodt reaction is known, in which an alkylarylketone is converted to the amide or the ammonium salt of the corresponding omega-aryl-alkanoic acid by reaction with ammonium polysulphide. In fact, the rearrangement of the aryl groups always occurs on the carbon atom which is farthest from the carbonyl group, and not, as in the process of the present invention, on the carbon atom in alpha position with respect to the carbonyl group. Furthermore, the yields are insufficient for practical purposes and the starting compound is an alkylarylketone instead of a haloketone.

Another rearrangement reaction starting from acylic halides leads to the arylacetic acids by reaction with diazomethane and successive hydrolysis in the presence of Ag$_2$O. That reaction comprises the use of diazomethane and the forming of a diazo-ketone, which are explosive compounds compatible with difficulty with a practical industrial process. Besides, the reaction is described as being irregular and providing variable yields.

The rearrangement of alkylarylketones to methyl esters of arylacetic acids by means of thallium salts has been described, but also in this case the method cannot be considered as interesting from the practical, commercial viewpoint due to the high toxicity of the thallium salts employed.

The mechanism of the dehalogenation of 1-benzoyl-1-bromo-cyclohexane by means of AgSbF$_6$ in alcohols, which leads to an ethylene ketone and in part to a transposition ester 1-phenyl-1-carboxyalkyl-cyclohexane, has also been described. That is the study of the dehalogenation of a particular tertiary aryl alpha-haloketone, while, on the other hand, it has been explicitly stated in literature that in the presence of primary or secondary alpha-haloketones no rearrangement reactions catalyzed by silver ions in alcohols occur.

Finally, the obtainment of 2-methyl-2-phenylpropionic acid by rearrangement of alpha-bromoisobutyrophenone with AgClO$_4$, either in the presence or in the absence of perchloric acid has been described. The description deals with the mechanics of the process, and also explicitly states that the rearrangement does not occur with primary and secondary alpha-haloketones independently of the presence of the perchloric acid, but only with the tertiary alpha-haloketone.

The previously known methods summarized herein, and in particular in British Pat. No. 1,211,134, are different from the present method and have few possibilities of use on an industrial scale due to the plurality and/or complexity of the required production steps, or the sophistication of the starting materials, or the generally relatively low yields.

THE PRESENT INVENTION

One object of this invention is to provide a simple and economical process for preparing arylacetic acid esters by rearrangement of the corresponding alpha-haloketones in a single step and which is free of the drawbacks and disadvantages of the prior art methods.

Another and specific object of the invention is to provide a simple and economical process for the preparation of the pharmaceutical product, 2-(6'-methoxy-2'-naphthyl)-propionic acid (+), preferably starting from 1-(6'-methoxy-2'-naphthyl)-2-chloro-1-propanone, the latter, an intermediate compound, being new in the art and within the scope of this invention.

These and other objects, which will more clearly appear to those skilled in the art from the description given hereinafter, are achieved by this invention in accordance with which the esters of arylacetic acids having the general formula:

in which
- Ar is an aryl or substituted aryl group containing from 6 to 30 carbon atoms;
- R is hydrogen, an alkyl group or substituted alkyl group containing from 1 to 10 carbon atoms; and
- R' is the residue of a monovalent or polyvalent alkyl or cycloalkyl alcohol containing from 1 to 10 carbon atoms, are obtained by reacting alpha-haloalkylaryl ketones of the general formula

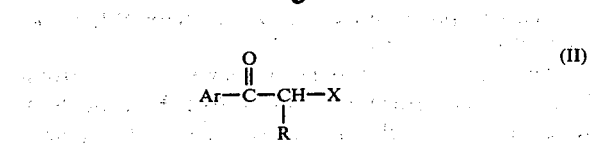

in which:
Ar and R have the same meaning as in formula (I); and
X is chlorine, bromine or iodine,
with substantially stoichiometric amounts of an Ag compound in an alcoholic medium R'OH in which R' is the same as in formula (I) and in the presence of an acid, at a temperature ranging from 0° C. to the boiling point of the reaction medium, and at substantially ambient pressure.

The corresponding acids are obtainable from the esters by simple, known techniques, such as basic hydrolysis.

In respect to the prior art in general the success of the process of this invention is surprising since, according to the art, arylacetic acid esters, or the acids, cannot be prepared in the presence of R groups in formula (I) different from hydrogen (Willgerodt), or that is impossible starting with primary or secondary haloketones.

The process can be schematically represented by the following reaction:

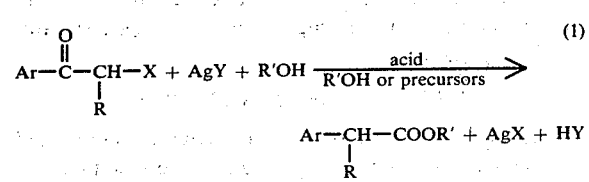

in which Y is the anion of a silver salt, the acid is as defined below, and the other symbols have the meanings already specified herein.

More specifically, the present process consists in reacting an Ag salt with the aryl alpha-haloketone (II) in an alcoholic medium R'OH in the presence of an acid at substantially room temperature.

In this way, for example, it is possible to obtain the following products, which are particularly useful in pharmacy.

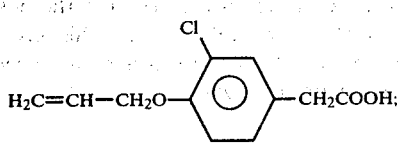

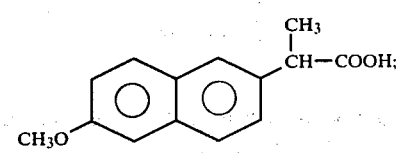

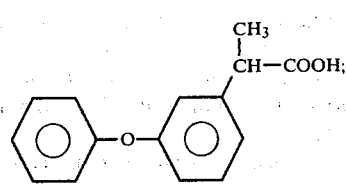

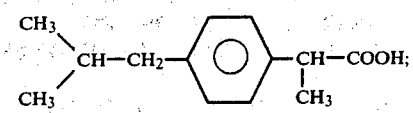

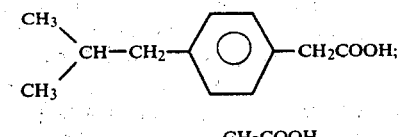

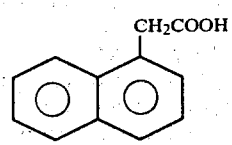

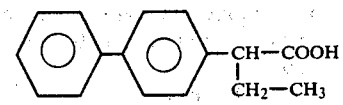

The acidity of the reaction medium developing from the beginning of reaction (1) is sufficient for the most reactive alpha-haloketones (II) to ensure the selective formation of the arylacetic ester (I). Nevertheless, in the presence of particular aryl alpha-haloketones (II) or of alcohols R'OH, and in general to improve the yields, it is advisable to additionally employ an acid in the reaction medium, so that the formation of by-products, such as alpha-ketoethers, etc., is reduced to negligible values.

Reaction (1), conducted according to the parameters specified hereinbefore, selectively and unexpectedly leads to the obtainment of the arylacetic esters of formula (I) starting from aryl alpha-haloketones of formula (II) through the rearrangement of the aryl group on the primary or secondary carbon atom in alpha position with respect to the carbonyl group of the alkylarylhaloketone (II), independently of the presence of other possible free positions, contrary to what is described in, or suggested by, the prior art.

The aryl alpha-haloketones of formula (II) are known compounds available on the market, or they can be prepared by known or conventional techniques.

For example, the ketone is prepared by reacting the aryl with the desired acyl chloride or substituted acyl chloride in nitrobenzene and in the presence of acid catalysts of the type of the Lewis acids (AlCl3, SnCl4, etc.), and the alpha-halo-derivative of formula (II) is obtained from the resulting alkylarylketone by conventional halogenation in a solvent, e.g., CCl4 or the like.

The preparation of 2-(6'-methoxy-2'-naphthyl)-propionic acid (+), as illustrative, represents a typical synthesis starting from 2-methoxy-naphthalene according to the process of the present invention and is shown schematically as follows:

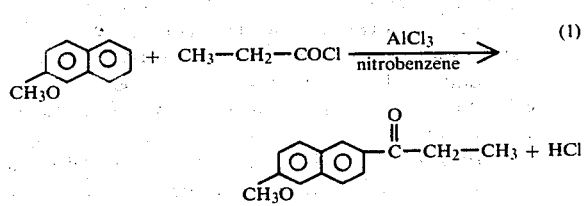

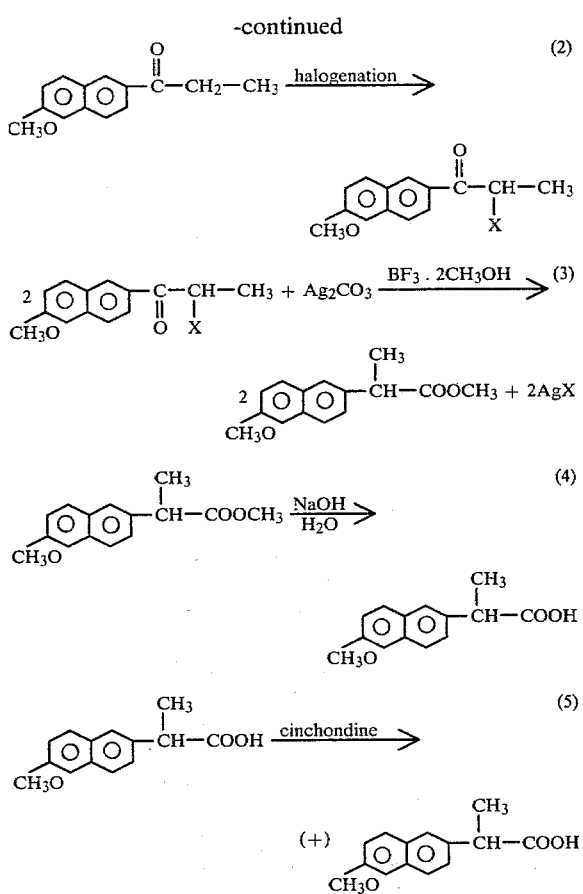

In reactions 2 and 3, X has the same meaning as in formula (II).

In equation (1), 1-(6'-methoxy-2'-naphthyl)-propanone is prepared from 2-methoxynaphthalene according to conventional methods by reaction with propionyl chloride in nitrobenzene or methylene chloride and in the presence of AlCl₃, as described hereinbefore.

In equation (2), 1-(6'-methoxy-2'-naphthyl)-2-halo-1-propanone is obtained from the compound formed in reaction (1) by conventional halogenation. For example, when X is Br, the halogenation is conducted in organic solvents, such as tetrahydrofurane, methanol, with bromine or other bromine donor agents. When X is Cl, the halogenation is conducted with a mixture in an organic solvent (dimethylformamide, ethyl acetate) of LiCl/CuCl₂, at a temperature ranging approximately from 50° to 90° C.

The resulting chloroderivative of formula (III):

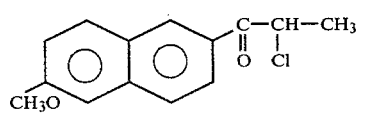

i.d., 1-(6'-methoxy-2'-napthyl)-2-chloro-1-propanone, is a new compound, is within the scope of the present invention, and is characterized in Example 20.

Equation (3) represents the reaction conducted according to the present invention.

Equations (4) and (5) respectively represent the alkaline hydrolysis (NaOH) leading to the racemic acid (equation 4) and the resolution thereof with cinchonidine (equation 5) to the desired 2-(6'-methoxy-2'-naphthyl)-propionic acid (+) by conventional techniques.

4'-methoxy-2-bromoacetophenone, alpha-bromoacetophenone, 1-(2'-naphthyl)-2-bromoethanone, 1-(1'-naphthyl)-2-bromoethanone, 1-(6'-methoxy-2'-naphthyl)-2-bromo-1-propanone, 1-(6'-methoxy-2'-naphthyl)-2-chloro-1-propanone, 1-(4'-methoxyphenyl)-2-bromo-1-butanone, 1-(4'-phenylphenyl)-2-bromo-1-butanone, 1-(3'-phenoxyphenyl)-2-bromo-1-propanone, etc., have proved to be efficient alpha-haloketones.

The reaction is conducted in an alcoholic medium. The alcohols are selected from among the alkyl and cycloalkyl alcohols having up to 10 carbon atoms, or the precursors thereof. The term "precursors", whenever used herein, means compounds which, under the reaction conditions and without interfering with said reaction, produce the alcohol R'OH required.

Methyl and ethyl alcohols have proved to be efficient R'OH alcohols; efficient precursors are alkyl orthoformiates, acetone dimethylacetal, the BF₃.2CH₃OH complex, the last compound having also the acid function.

BF₃.2CH₃OH is a commercial product easily available on the market and in any case obtainable from BF₃ and methanol.

Ag salts of organic and/or inorganic anions, also in admixture with one another, and Ag oxide are employed.

Efficacious results have been obtained by using at least an Ag salt selected from among silver acetate, AgSbF₆ (silver hexafluoroantimoniate), silver nitrate, AgBF₄ (silver tetrafluoroborate), AgClO₄ (silver perchlorate), AgCF₃SO₃ (silver trifluoromethanesulphonate), silver carbonate, silver sulphate or the oxide.

The acid employed is preferably selected from the Lewis acids in general, BF₃ (boron trifluoride), CF₃SO₃H (trifluoromethanesulphonic acid), HBF₄ (fluoroboric acid) CH₃SO₃H (methanesulphonic acid), H₂SO₄, complexes BF₃.2CH₃COOH, HBF₄. Et₂O (etherated fluoroboric acid), complex BF₃.Et₂O (ethyl boro-ether trifluoride) and, advantageously, complex BF₃.2CH₃OH which, in the reaction conditions, behaves both as an acid and as a source of alcohol CH₃OH.

Generally it is possible to employ the acids, the silver salt of which is at least partially soluble in the reaction medium. The reaction is conducted, as explained hereinabove, in the presence of an excess of alcohol R'OH or of its precursor, which constitutes the reaction medium besides acting as a reagent.

Nevertheless the process is consistent with the use, when desired, of such inert solvents as e.g., CH₂Cl₂, dichlorobenzene, acetonitrile, etc.

The reaction is conducted in a conventional inert atmosphere such as N₂, argon, etc., and preferably in the absence of light. In such case the concentration can vary over a wide range, which is not critical for the reaction.

The quantitative ratios between the starting aryl alpha-haloketone (II) and the Ag salt are substantially maintained according to the stoichiometry of the reaction, efficient values being comprised between about 0.2 and 2 moles of Ag salt or oxide for 1 mole of alpha-haloketone (II). At the conclusion of the reaction, the reacted silver is recovered as AgX halide and is regenerated and recycled according to conventional methods, while the portions, if any, of unreacted Ag salt are recovered by acidification (HCl), etc.

Alcohol R'OH or its precursor is employed in a molar ratio ranging approximately from 1 to 200 moles for 1 mole of alpha-haloketone (II).

Finally, the acid is utilized in a molar ratio in respect of alpha-haloketone (II) ranging approximately from 0.05 to 200 moles for 1 mole of haloketone.

The temperature, as indicated hereinbefore, ranges from 0° C. to the boiling point of the mixture; preferably it is room temperature.

Reaction times of the order of 5 minutes up to 24 hours are usually sufficient to allow the completion of the reaction, depending on the remaining parameters selected. The process is preferably conducted as follows:

The alcohol and successively the Ag salt and the acid are introduced into a thermoregulated reactor equipped with a stirrer and a charging system of the reagents. The aryl alpha-haloketone (II) is then added, in the desired ratios, to the mixture obtained. The reaction is conducted at substantially room temperature up to the conclusion. After filtering, the mixture is diluted with $H_2O$ and extracted with ether, whereupon the extract is washed and dried, etc. The acid is then obtained by basic hydrolysis (NaOH) of the ester.

In particular, according to the present invention, 2-(6'-methoxy-2'-naphthyl)-propionic acid (+) is obtained from the racemic acid prepared according to the present invention by conventional separation methods, such as treatment with cinchonidine, dihydrocinchonine, etc.

The process, due to the mild operating conditions and the high selectivity of the product obtained, appears particularly advantageous.

The following examples are given to illustrate the invention in more detail and are not intended as limiting.

Examples 2 and 19 are comparative tests conducted without using acids. As clearly appears, the acid yields are much lower and the ether by-product results prevailingly, the reaction times being longer.

EXAMPLE 1

Silver trifluoromethane-sulphonate (3 g; 11.6 m.moles), trifluoromethane-sulphonic acid (6 g; 40 m.moles) were added, in a nitrogen atmosphere, to 10 ml of methanol. 4'-methoxy-2-bromoacetophenone (2.3 g; 10 m.moles) were added to the suspension so obtained. The mixture was magnetically stirred, in the absence of light, in a nitrogen atmosphere and at 15° C. for 2 hours.

The reaction mixture was then filtered and diluted with water. It was extracted with ethyl ether, the ether extract was washed with water, dried on anhydrous sodium sulphate and then evaporated.

By basic hydrolysis with aqueous soda at 50% in methanol, 4'-methoxy-phenylacetic acid (1.2 g) was obtained from the reaction raw product with a yield of 75% calculated on the starting ketone.

EXAMPLE 2

(Comparative Test)

Example 1 was repeated except that the reaction was conducted in the absence of acid.

By basic hydrolysis of the raw reaction product, it was possible to obtain 4'-methoxy-phenylacetic acid (0.45 g) with a yield of 27% calculated as in Example 1.

EXAMPLE 3

4'-methoxy-2-bromoacetophenone (230 mg; 1 m.mole) was added to a solution of silver trifluoromethane-sulphonate (308 mg; 1.2 m.moles) in trimethylorthoformiate (2 ml). The mixture was magnetically stirred in the absence of light, in a nitrogen atmosphere at 15° C. for 4 hours.

The reaction mixture was then treated as described in Example 1.

The gas chromatographic analysis of the raw reaction product revealed that 37% of the charged product was converted into methyl 4'-methoxy-phenylacetate.

EXAMPLE 4

Alpha-bromoacetophenone (1 g; 5 m.moles) was dissolved, in a nitrogen atmosphere, in 10 ml of trimethylformiate. Trifluoromethane-sulphonic acid (0.85 g; 5 m.moles) and silver trifluoromethane-sulphonate (1.5 g; 5.8 m.moles) were added to the solution. The mixture was then magnetically stirred, in the absence of light, in a nitrogen atmosphere, at 15° C. for 24 hours. Thereafter, the reaction mixture was treated as described in Example 1.

Phenylacetic acid (0.14 g) with a yield of 20% calculated as in Example 1 was obtained by basic hydrolysis of the raw reaction product.

EXAMPLE 5

Alpha-bromoacetophenone (1 g; 5 m.moles) was dissolved in a nitrogen atmosphere in 10 ml of trimethylorthoformiate. The solution was added with silver tetrafluoroborate (1.2 g; 5.8 m.moles) and $BF_3.2CH_3OH$ (0.66 g; 5m.moles). The mixture was magnetically stirred in the absence of light, in a nitrogen atmosphere, at 50° C. for 1 hour and 30 minutes.

The reaction mixture was then treated as described in Example 1.

By basic hydrolysis of the raw product, phenylacetic acid (0.28 g) was obtained with a yield of 42% calculated as in Example 1.

EXAMPLE 6

1-(2'-naphthyl)-2-bromoethanone (1.25 g; 5 m.moles) was dissolved, in a nitrogen atmosphere, in 10 ml of trimethylorthoformiate. Silver tetrafluoroborate (1.2 g; 5.8 m.moles) and $BF_3.2CH_3OH$ (0.66 g; 5 m.moles) were added to the solution. The mixture was the magnetically stirred, in the absence of light, in a nitrogen atmosphere, at 50° C., for 1 hour and 15 minutes.

The reaction mixture was treated as described in Example 1.

By basic hydrolysis of the raw reaction product, 2-naphthyl-acetic acid (0.26 g) with a yield of 28% calculated as in Example 1 was obtained.

EXAMPLE 7

1-(6'-methoxy-2'-naphthyl)-2-bromo-1-propanone (1.47 g; 5 m.moles) was dissolved, in a nitrogen atmosphere, in 10 ml of trimethylorthoformiate. The solution was added with silver tetrafluoroborate (1.2 g; 5.8 m.moles) and $BF_3.2CH_3OH$ (0.66 g; 5 m.moles). The mixture was magnetically stirred, in the absence of light, in a nitrogen atmosphere, at 30° C., for 3 hours.

The reaction mixture was then treated as described in Example 1.

By basic hydrolysis of the raw product, 2-(6'-methoxy-2'-naphthyl)-propionic acid (0.52 g) with a yield of 45% calculated as in Example 1 was obtained.

EXAMPLE 8

1-(6'-methoxy-2'-naphthyl)-2-bromo-1-propanone (1.47 g; 5 m.moles) and silver tetrafluoroborate (1.2 g; 5.8 m.moles) were added, in a nitrogen atmosphere, to 10 ml of $BF_3.2CH_3OH$. The resulting mixture was magnetically stirred, in the absence of light, in a nitrogen atmosphere, at 15° C., for 1 hour.

The reaction mixture was then treated as described in Example 1.

By basic hydrolysis of the raw reaction product, 2-(6'-methoxy-2'-naphthyl)-propionic acid (0.75 g) was obtained with a yield of 70% calculated as in Example 1.

EXAMPLE 9

Silver carbonate (0.83 g; 3 m.moles) was dissolved in 10 ml of $BF_3.2CH_3OH$, whereupon 1-(6'-methoxy-2'-naphthyl)-2-bromo-1-propanone (1.47 g, equal to 5 m.moles) was added, in a nitrogen atmosphere, to the solution. The mixture so obtained was magnetically stirred, in the absence of light, in a nitrogen atmosphere, at 15° C., for 1 hour and 30 minutes.

The reaction mixture was then treated as described in Example 1.

By basic hydrolysis of the raw reaction product, 2-(6'-methoxy-2'-naphthyl)-propionic acid (0.82 g), with a yield of 75% calculated as in Example 1, was obtained.

The resulting racemic 2-(6'-methoxy-2'-naphthyl)-propionic acid was dissolved in a mixture of 15 ml of methanol and 3.5 ml of acetone.

Cinchonidine (1.07 g) was dissolved in a mixture of 11 ml of methanol and 7 ml of acetone.

The two hot solutions were mixed with each other and allowed to cool to room temperature. The salt that precipitated was filtered and recrystallized from a mixture of methanol and acetone, then it was shaken in a mixture of dilute HCl and benzene to obtain the free acid. By evaporation of the organic layer, 0.2 g (yield=49% of the theoretical value) of 2-(6'-methoxy-2'-naphthyl)-propionic acid (+) with $[\alpha] = +66°$ were obtained.

EXAMPLE 10

Silver acetate (0.97 g, equal to 5.8 m.moles) was dissolved in 10 ml of $BF_3.2CH_3OH$. 1-(6'-methoxy-2'-naphthyl)-2-bromo-propanone (1.47 g, equal to 5 m.moles) was added, in a nitrogen atmosphere, to the solution. The resulting mixture was magnetically stirred, in the absence of light, in a nitrogen atmosphere, at 15° C., for 1 hour and 30 minutes.

The reaction mixture was then treated as described in Example 1.

By basic hydrolysis of the raw reaction product, 2-(6'-methoxy-2'-naphthyl)-propionic acid (0.7 g) was obtained, the yield being 65% calculated as in Example 1.

EXAMPLE 11

Silver oxide (0.7 g; 3 m.moles) was dissolved in 10 ml of $BF_3.2CH_3OH$. 1-(6'-methoxy-2'-naphthyl)-2-bromo-1-propanone (1.47 g; 5 m.moles) was added, in a nitrogen atmosphere, to the solution. The mixture so obtained was magnetically stirred, in the absence of light, in a nitrogen atmosphere, at 15° C., for 1 hour and 30 minutes.

The reaction mixture was then treated as described in Example 1.

By basic hydrolysis of the raw reaction product, 2-(6'-methoxy-2'-naphthyl)-propionic acid (0.7 g), with a yield of 65% calculated as in Example 1, was obtained.

EXAMPLE 12

Operations were as described in Example 9, but using a lesser amount of $BF_3.2CH_3OH$ (3.3 ml).

by basic hydrolysis of the raw reaction product, 2-(6'-methoxy-2'-naphthyl)-propionic acid (0.7 g), with a yield of 65% calculated as in Example 1, was obtained.

EXAMPLE 13

Silver carbonate (0.83 g; equal to 3 m.moles) was dissolved in 3.3 ml of $BF_3.2CH_3OH$, whereupon 1-(6'-methoxy-2'-naphthyl)-2-chloro-1-propanone (1,245 g, equal to 5 m.moles) was added, in a nitrogen atmosphere, to the solution. The mixture so obtained was magnetically stirred, in the absence of light, in a nitrogen atmosphere, at 40° C., for 8 hours.

The reaction mixture was then treated as described in Example 1.

By basic hydrolysis of the raw reaction product, 2-(6'-methoxy-2'-naphthyl)-propionic acid (0.61 g), with a yield of 55% calculated as in Example 1, was obtained.

EXAMPLE 14

Example 1 was repeated, but conducting the reaction in ethanol (10 ml) instead of in methanol.

By basic hydrolysis of the raw reaction product, 4'-methoxy-phenylacetic acid (0.69 g) with a yield of 42% calculated as in Example 1 was obtained.

EXAMPLE 15

Silver carbonate (0.83 g; 3m.moles) was dissolved in 10 ml of $BF_3.2CH_3OH$, whereupon 1-(4'-methoxy-phenyl)-2-bromo-1-butanone (1.29 g, equal to 5 m.moles) was added, in a nitrogen atmosphere, to the solution. The resulting mixture was magnetically stirred, in the absence of light, in a nitrogen atmosphere, at 15° C. for 1 hour and 30 minutes.

The mixture was then treated as described in Example 1.

By basic hydrolysis of the raw reaction product, 2-(4'-methoxy-phenyl)-butanoic acid (0.5 g) with a yield of 52% calculated as in Example 1 was obtained.

EXAMPLE 16

1-(1'-naphthyl)-2-bromoacetone (1.25 g, equal to b 5 m.moles) was dissolved, in a nitrogen atmosphere, in 10 ml of trimethyl-orthoformiate. Silver tetrafluoroborate (1.2 g, equal to 5.8 m.moles) and $BF_3.2CH_3OH$ (0.66 g, equal to 5 m.moles) were added to the solution. The mixture was magnetically stirred, in the absence of light, in a nitrogen atmosphere at 50° C. for 1 hour and 30 minutes.

The reaction mixture was then treated as described in Example 1.

By basic hydrolysis of the raw reaction product, 1-naphthylacetic acid (0.23 g) with a yield of 25% calculated as in Example 1 ws obtained.

EXAMPLE 17

Silver carbonate (0.83 g, equal to 3 m.moles) was dissolved in 10 ml of BF$_3$.2CH$_3$OH, whereupon 1-(3'-phenoxyphenyl)-2-bromo-1-propanone (1.53 g, 5 m.moles) was added, in a nitrogen atmosphere, to the solution. The mixture so obtained was magnetically stirred, in the absence of light, in a nitrogen atmosphere, at 15° C., for 2 hours.

The reaction mixture was then treated as in Example 1.

By basic hydrolysis of the raw reaction product, it was possible to obtain 2-(3'-phenoxyphenyl)-propionic acid. The product was identified by comparison with a known sample.

EXAMPLE 18

Silver carbonate (0.5 g, equal to 18 m.moles) was dissolved in 30 ml of BF$_3$.2CH$_3$OH, whereupon 1(4'-phenylphenyl)-2-bromo-1-butanone (9.1 g, equal to 30 m.moles) was added, in a nitrogen atmosphere, to the solution. The resulting mixture was magnetically stirred, in the absence of light, in a nitrogen atmosphere, at 15° C., for 20 hours.

The reaction mixture was then treated as described in Example 1.

By basic hydrolysis of the raw reaction product, 2-(4'-phenylphenyl)-butanoic acid (2.9 g) with a yield of 41% calculated as in Example 1 was obtained.

EXAMPLE 19

(Comparative Test)

1-(6'-methoxy-2'-naphthyl)-2-bromo-1-propanone (1.47 g, equal to 5 m.moles) and silver tetrafluoroborate (1.2 g, equal to 5.8 m.moles) were added, in a nitrogen atmosphere, to 10 m. of methanol. The mixture so obtained was magnetically stirred, in the absence of light, in a nitrogen atmosphere, at 15° C., for 24 hours.

The reaction mixture was then treated as described in Example 1.

The raw reaction product contained 1-(6'-methoxy-2'-naphthyl)-2-methoxy-1-propanone (0.66 g, yield=55% calculated as in Example 1, melting point=58°-60° C.; 2-(6'-methoxy-2'-naphthyl)-propionic acid (0.195 g, yield=17% calculated as in Example 1.

EXAMPLE 20

Synthesis of 1-(6'-methoxy-2'-naphthyl)-2-chloro-1-propanone (III)

Dihydrated chloride (12.28 g, equal to 0.072 moles), lithium chloride (1.53 g, equal to 0.036 moles) and 20 ml of N,N-dimethylformamide were introduced into a 3-neck flask having a 50 ml capacity, equipped with a magnetic stirrer, a thermometer and a bubble cooler.

After heating the mixture to 80° C., 1-(6'-methoxy-2'-naphthyl)-1-propanone (6.45 g, equal to 0.03 m.moles) was added. Stirring was conducted for 2 hours at 80°-90° C. Then the reaction mixture was poured onto ice, it was acidified with hydrochloric acid to dissolve the copper chloride, which precipitated. It was extracted with ether, the ether extract was washed with water, dried with anhydrous sodium sulphate and evaporated. 6.63 g of product (III) (yield=89%), which was crystallized in ethanol (melting point=77°-80° C.), were obtained. The elemental, NMR, IR and mass analyses confirm the structure proposed (III).

What we claim is:

1. A process for preparing the arylacetic esters of formula (I):

wherein:
Ar is a C$_6$–C$_{30}$ aryl group or substituted aryl group;
R is a hydrogen atom or a C$_1$–C$_{10}$ alkyl group or substituted alkyl group; and
R' is the residue of a mono- or polyvalent alkyl or cycloalkyl alcohol having up to 10 carbon atoms;
characterized in that an alpha-halo-alkylarylketone of formula (II):

wherein:
Ar and R have the same meaning as in formula (I); and
X is selected from the group consisting of chlorine, bromine and iodine,
is reacted with at least an Ag compound in an alcoholic medium of formula R'OH, in which R' has the same meaning as in formula (I), and in the presence of an acid, at a temperature ranging from 0° C. to the boiling point of the reaction mixture and at a pressure substantially equal to the ambient pressure.

2. The process according to claim 1, in which the Ag compound is a salt of an organic and/or inorganic acid.

3. The process of claim 2, in which the Ag compound is selected from the group consisting of the acetate, nitrate, carbonate, sulphate, hexafluoroantimoniate, tetrafluoroborate, perchlorate, trifluoromethanesulphonate, or is the silver oxide.

4. The process according to claim 1, in which the alcoholic medium R'OH is selected from the group consisting of the mono- and polyvalent alkyl and cycloalkyl alcohols having up to 10 carbon atoms, and precursors thereof.

5. The process according to claim 4, in which the alcoholic medium is selected from the group consisting of methyl alcohol and ethyl alcohol.

6. The process according to claim 4, in which the alcoholic precursor medium is selected from the group consisting of alkyl orthoformiates, acetone dimethylacetal and the complex BF$_3$.2CH$_3$OH.

7. The process according to claim 1, in which the acid is an acid the silver salt of which is at least partially soluble in the reaction medium.

8. The process according to claim 7, in which the acid is selected from the group consisting of the Lewis acids, boron trifluoride, trifluoromethanesulphonic acid, fluoroboric acid, methanesulphonic acid, sulphuric acid, etherated fluoroboric acid and the acid complexes BF$_3$.2CH$_3$OH; BF$_3$.2CH$_3$COOH; and BF$_3$.(C$_2$H$_5$)$_2$O.

9. The process according to claim 1, in which about 0.2 to 2 moles of Ag compound per 1 mole of the starting alpha-halo-alkylarylketone (II) are employed.

10. The process according to claim 1, in which the alcoholic medium of formula R'OH or the precursor thereof is employed in a molar ratio comprised between 1 and about 200 moles per 1 mole of starting alpha-haloalkylarylketone (III).

11. The process according to claim 1, in which the acid is employed in a molar ratio comprised between 0.05 and about 200 moles per 1 mole of starting alpha-halo-alkylarylketone (II).

12. The process according to claim 1, in which the alpha-haloalkylarylketone of formula (II) is selected from the group consisting of 4'-methoxy-2-bromoacetophenone, alpha-bromoacetophenone, 1-(2'-naphthyl)-2-bromoethanone, 1-(1'-naphthyl)-2-bromoethanone, 1-(6'-methoxy-2'-naphthyl)-2-bromo-1-propanone, 1-(6'-methoxy-2'-naphthyl)-2-chloro-1-propanone, 1-(4'-methoxy-phenyl)-2-bromo-1-butanone, 1-(3'-phenoxyphenyl)-2-bromo-1-propanone, 1-(4'-phenylphenyl)-2-bromo-1-butanone.

13. A process for preparing the methyl or ethyl esters of 2-(6'-methoxy-2'-naphthyl)-propionic acid which comprises reacting 1-(6'-methoxy-2'-naphthyl)-2-halo-1-propanone, in which the halogen is chlorine, bromine or iodine, with substantially stoichiometric amounts of at least an Ag compound in an alcoholic medium selected from the group consisting of methyl and ethyl alcohol and the precursors thereof, at a temperature comprised between 0° C. and the boiling point of the reaction mixture, in the presence of acids.

14. The process according to claim 1, in which the reaction is conducted in the presence of a solvent.

15. The process of claim 14, in which the solvent is selected from the group consisting of dichlorobenzene, acetonitrile and dichloromethane.

16. The process according to claim 1, in which the reaction is conducted in an inert atmosphere, substantially in the absence of light.

17. The process according to claim 1 wherein the esters of the arylacetic acids (I) are subsequently hydrolyzed to the corresponding acids.

18. The process, wherein the methyl and ethyl esters of 1-(6'-methoxy-2'-naphthyl)-propionic acid, obtained according to the process of claim 1, for preparing 1-(6'-methoxy-2'-naphthyl)-propionic acid in the isomeric form (+) by basic hydrolysis and successive separation with an alkaloid.

* * * * *